United States Patent [19]

Kahán née László et al.

[11] 4,418,060
[45] Nov. 29, 1983

[54] THERAPEUTICALLY ACTIVE COMPLEXES OF TETRACYCLINES

[75] Inventors: Ilona Kahán née Laszlo, Budapest; Helga Hammer; Ilona Béládi, both of Szeged, all of Hungary

[73] Assignee: Medimpex Gyógyszerkülkereskedelmi Vállalat, Budapest, Hungary

[21] Appl. No.: 76,337

[22] Filed: Sep. 17, 1979

Related U.S. Application Data

[63] Continuation of Ser. No. 862,343, Dec. 20, 1977, abandoned, which is a continuation-in-part of Ser. No. 784,840, Apr. 4, 1977, abandoned, which is a continuation of Ser. No. 302,667, Nov. 1, 1972, abandoned.

[30] Foreign Application Priority Data

Sep. 6, 1971 [GB] United Kingdom ............... 41533/71

[51] Int. Cl.$^3$ ............................................. C07C 103/19
[52] U.S. Cl. .................................... 424/227; 424/315; 424/319; 424/30; 260/351.1; 260/351.2; 260/352.3; 260/351.4
[58] Field of Search ............ 260/559 AT, 513 N, 351, 260/351.1, 351.2, 351.3, 351.4; 424/227, 315, 319, 330

[56] References Cited

FOREIGN PATENT DOCUMENTS 2243776 3/1973 Fed. Rep. of Germany .
1401178 7/1975 United Kingdom .

OTHER PUBLICATIONS

Kahan et al., Chem. Abst. 79 (1973) #78469h.
Kahan et al., Chem. Abst. 82 (1957) #182d.

*Primary Examiner*—Arthur P. Demers

[57] ABSTRACT

Tri-tetracyclines are complexes of tetracyclines with an amino compound containing per molecule at least a tris (hydroxyalkyl) group and at least a primary or secondary amino group in a molar excess in respect to the tetracycline compound. The complexes have high water solubility and are particularly useful for parenteral administration.

9 Claims, No Drawings

THERAPEUTICALLY ACTIVE COMPLEXES OF TETRACYCLINES

This application is a continuation of application Ser. No. 862,343, filed Dec. 20, 1977, now abandoned, which in turn was a continuation-in-part of Ser. No. 784,840, filed Apr. 4, 1977, now abandoned, which in turn was a continuation of Ser. No. 302,667, filed Nov. 1, 1972, now abandoned.

The present invention relates to therapeutically active water-soluble complexes of tetracyclines and to therapeutic preparations containing the same active substance. The new complexes exhibit a therapeutical activity, which is generally more favourable than that of the respective tetracycline.

Due to the synthesis and application of new derivatives the antibiotic range of activity of the compounds belonging to the group of tetracyclines keeps increasing. The active ingredient has to comply with more and more requirements from the point of view of potency and the attainable antibiotic level in the living organism. Because of resistance to some tetracycline-derivatives to overcome infections caused by some pathogenic bacteria new tetracycline derivatives, such as minocycline (7-dimethylamino-6-deoxy-6-demethyltetracycline), chelocardin (2-decarboxamido-2-acetyl-4-dedimethylamino-4-epiamino-9-methyl-5,6-anhydrotetracycline) were synthetised. Minocycline is effective against the tetracycline-resistant Staphylococcus and *E. coli* strains, whereas chelocardin is effective against the tetracycline-resistant Proteus strains.

Minocycline is to a great extent lipid soluble, chelocardin is moderately lipid soluble and its water solubility is lower than that of other tetracyclines.

The oral administration of tetracyclines is, as known, accompanied by gastrointestinal complaints and in case of some tetracyclines a severe renal injury can be observed depending on the absorbed amount of the relatively large dose administered per os. Though the dose administered daily per os was decreased in the case of methacycline to 600 to 900 mg., in the case of doxycycline to 100 to 200 mg. against the daily dose of 2 g. in the case of tetracycline or oxytetracyline, even so renal injuries can be observed in the case of methacycline and gastrointestinal disorders can be observed in the case of both tetracycline types. In addition administration per os is impossible in conditions of severe diseases, during operations, such as in the course of thoracic surgery.

Thus there is a continuous need for aqueous tetracycline solutions of high concentration and high therapeutic activity being neutral, free of tissue damaging effect, suitable for intravenous, intramuscular and local administration, such as intraocular injection in ophthalmology.

Compounds falling under the group of tetracyclines are amphoteric, and though they are soluble in aqueous bases or in acids, but near to their isoelectric point—in the physiological pH range—their water solubility is very low.

To overcome the difficulties mentioned above, the preparation of the piperazine complex of tetracyclines has been suggested in U.S. Pat. No. 3,347,861 (1967) and the piperazine and morphine derivatives of the tetracycline have been suggested in Farmaco, Ed. sci. 21, 775–84, 1966 by Valcavi, U. Bolego, Z. et al. The piperazine derivatives, however, may cause cataract and the deleterious pharmacological effects of morphine are known. The N-(1-carbamyl-3-methyl-thio-propylamin methyl)-tetracycline derivative formed with methionine amide is disclosed in the U.S. Pat. No. 3,461,161. This compound is prepared from the tetracycline base which is much less stable than the tetracycline hydrochloride, the preparation is however rather complicated from technological point of view.

There are references concerning some storable ready for use solutions prepared from tetracycline-derivatives. For example a ready for use injection containing tissue damaging dimethylsulfoxide is described in U.S. Pat. No. 3,546,339 and polyvinylpirrolidone is described in Schoog et al.: Arzneimittelforschung 21, 1459 (1971). The presence of polyvinylpirrolidone prevents however the administration to people suffering from renal disease and dimethylsufoxide can cause cataract. The recently synthetised lipid soluble tetracyclines (methacycline, doxycycline, minocycline) can be administered in addition to the routes of administration mentioned above perorally or in a slow drip infusion in the form of the available acidic pharmaceutical preparations. There is a need for the preparation of new complexes of tetracyclines, which are water soluble in the entire physiological pH range ($p_K$=6.8–8.4), having high therapeutic activity, enhanced stability. An object of the present invention is to prepare complexes of tetracyclines having a water solubility with several order of magnitude higher, than that of the parent compound and at the same time the lipid solubility thereof does not change substantially. The lipid solubility is of great importance as the antibiotic level in the tissue is in direct proportion to the measured distribution quotient of the antibiotic between water and chloroform. Thus new complexes had to be prepared and applied therapeutically, which under increasing water-solubility show substantially unchanged lipid/water distribution quotient and thus both the in vivo and in vitro tested antibiotic properties thereof are particularly favourable.

According to the invention complexes complying with the requirements mentioned above can be prepared by combining compounds belonging to the group of tetracyclines with amino gcompounds containing per molecule at least a tris (hydroxyalkyl) group and at least a primary or secondary amino group in a molar excess as to the tetracycline compound.

The following compounds and salts thereof resp. belonging to the tetracycline (TC) group can be used for the preparation of the tetracycline complexes: tetracycline.

oxytetracycline (5-hydroxytetracycline) (OTC)
methacycline (6-methylene-5-hydroxytetracycline) (MOTC)
doxycycline (6-deoxy-5-hydroxytetracycline) (DOOTC)
minocycline (7-dimethylamino-6-deoxy-6-demethyltetracycline) (MINO)
demethylchlortetracycline (6-demethyl-7-chlortetracycline)
chlortetracycline (7-chloro-tetracycline)
chelocardin (2-decarboxamido-2-acetyl-4-dedimethylamino-4-epiamino-9-methyl-5a,6-anhydrotetracyline)

In addition to tris-(hydroxymethyl)aminomethane the following amino compounds are preferred:
1,3-bis[tris(hydroxymethyl)methylamino]-propane
N-tris(hydroxymethyl)methyl-3-aminopropane sulfonic acid N-tris[hydroxymethyl]methyl-2-aminoethane sulfonic acid
N-tris(hydroxymethyl)methylglycine
and salts thereof.

When preparing the new complexes the amino compounds can be used due to their favourable buffering effect in excess related to the tetracycline. E.g. a 3- to 6-fold molar excess or even more can be used, without influencing unfavourably the therapeutical activity of the parent compound.

A three-fold molar excess of the amino compounds related to the tetracyclines is required because with a smaller amount the formation of the complex is inhibited. A six-fold molar excess exerts a stabilizing effect whereas an excess more than six-fold promotes the solvation and acts as a buffer substance.

The relatively wide $p_K$ range of the amino compounds referred to makes possible to use amino compounds in combination with tetracyclines with different pH values. In the case of storable ready for use injections complexes including alkali earth metals stable in a high pH range an amino compound of higher $p_K$ value e.g. tris(hydroxymethyl)aminomethane ($p_K$) 8.33, whereas in tetracycline complexes which are free of alkali earth metals, an amino compound of lower $p_K$ such as 1,3-bis-tris(hydroxymethyl)methylaminopropane ($p_K=6.8$) is to be used.

The tetracycline complexes are prepared by reacting an amino compound containing a tris(hydroxyalkyl) group or an aqueous or organic solution thereof with tetracycline or derivatives thereof, or with acid addition salts thereof formed with inorganic or organic acids or with an aqueous or organic solution of these tetracycline-derivatives.

The complexes of tetracyclines are water soluble, yielding solutions up to 10% concentration in the pH range 7.3–8.0, however, identical solutions may be obtained by merely dissolving the tetracyclines in Tris-buffer. Stable preconstituted parenteral formulations preferably include an antioxidant.

Inspite of the different lipid solubility of the tetracyclines and the complex forming agents, the new tetracycline complexes prepared have always a high water solubility.

When preparing pharmaceutical compositions containing the new complexes of the invention optionally polyhydroxy compounds and/or alkali metal salts and carriers, excipients and antioxidants conventionally added to parenteral pharmaceutical compositions can be added. The active ingredient concentration amounts to 2 to 10%.

Comparing the infra-red spectra of potassium bromide discs of the starting antibiotics and those of the products of the invention the data are the following:

(a) Starting from Oxytetracycline hydrochloride, its band at 678 cm$^{-1}$ of medium intensity disappeared or changed into a low shoulder; its weak band at 818 cm$^{-1}$ disappeared; its band at 1540 cm$^{-1}$ shifted to 1520 cm$^{-1}$; the bands at 1590 and 1625 cm$^{-1}$ changed into a shoulder at 1600 cm$^{-1}$ and a very intense band at 1636 cm$^{-1}$, the band at 1671 cm$^{-1}$, present in the starting material, was lacking from the product.

(b) Starting from Doxycycline (α-6-deoxy-5-oxytetracycline) a band of medium intensity at 660 cm$^{-1}$ and a shoulder 678 cm$^{-1}$ appeared instead of the double band of the starting material at 662 and 670 cm$^{-1}$, a weak band of 823 cm$^{-1}$ appeared replacing those of doxycycline at 818 cm$^{-1}$ and 828 cm$^{-1}$, and another one at 855 cm$^{-1}$. Instead of the band of the starting material at 849 cm$^{-1}$, a new band of more than medium intensity appeared at 1513 cm$^{-1}$.

(c) In the case of Methacycline (6-methylene-5-hydroxy-tetracycline hydrochloride) its band at 653 and 677 cm$^{-1}$ were replaced by a shoulder at 645 cm$^{-1}$. The intensities of the bands at 820 and 840 cm$^{-1}$, decreased, and instead of the band of methacycline at 873 cm$^{-1}$ another weak one appeared at 860 cm$^{-1}$. A new band of medium intensity presented itself at 1512 cm$^{-1}$.

(d) In the product obtained from Tris- and Chlorotetracycline hydrochloride a new weak band at 595 cm$^{-1}$ was discernible.

Optical rotation [$\alpha_D$] of Oxytetracycline equals $-120°$, that of Tri-oxytetracycline $-145°$.

Tri-tetracycline complexes of the invention can be identified by chromatography. Minocycline was subjected to thin layer chromatography on a Kieselgel G thin layer plate in a 50:10:10:10:10:10 solvent mixture containing benzene, methanol, ethanol, ethyl acetate, dimethylformamide and dimethylacetamide. $R_f$ of minocycline:0.16, whereas the $R_f$ value of the complex of minocycline formed with N-tris(hydroxymethyl)methylglycine is 0.63. Chelocardin was identified in a similar way, its $R_f$ value in the previous system is 0.21, whereas the $R_f$ value of the complex of chelocardin formed with N-tris(hydroxymethyl)methylglycine is 0.42. The $R_f$ value of minocycline hydrochloride on Kieselgel G thin layer plate in a 60:20:10:10 solvent system of benzene methanol, ethyl acetate and dimethylformamide is 0.1, whereas the $R_f$ value of the complex of minocycline with tris(hydroxymethyl)aminomethane is 0.2.

Complexes of tetracycline formed with the amino-compound mentioned above are called further on tri-tetracyclines. Biological activity of the tri-tetracyclines is equal or higher, than that of tetracyclines. Numerous Gram-positive and Gram-negative strains were tested and the in vitro minimal inhibitory concentration of tri-oxytetracycline, tri-methacycline and tri-doxycycline proved to be lower, the minimal inhibitory concentration of tri-minocycline and tri-chelocardin is identical with that of the parent compound. On testing the tissue damaging effect of the tri-tetracyclines no cell-damaging effect could be detected on the chicken's fibroblast culture.

Toxicity data LD$_{50}$ values of different tetracyclines and tri-tetracyclines are disclosed in Table I.

TABLE I

Toxicity data (LD$_{50}$) values of different Tetracyclines and Tri-tetracyclines in mice

| Tetracycline | Mode of administration (mg/kg) | | |
|---|---|---|---|
| | oral | intravenous | intravenous in the form of a Tri-complex |
| OTC | 2500 | — | 500 |
| Pyrrolidinomethyl-OTC | — | 120 | — |
| MOTC | — | — | 500 |
| MINO | 3100 | 170 | 500 |
| Chelocardine | — | — | 220 |

By administering tri-tetracyclines parenterally in animal-tests a high blood and tissue antibiotic level can be obtained. Intravenous administration of tri-doxycycline to humans yields an identical blood level as the administration of other polyvinylpirrolidone-containing preparations without the unpleasant side-effects (renal damaging and local phlebitis causing effect) of the polyvinylpirrolidone. According to the test-results the intravenous administration of tri-methacycline in a low dose yields the same blood level like a 4- to 5-fold per os amount. The intravenous administration of tri-minocycline in human therapy yields a high but a controlled blood level and the intramuscular administration thereof yields a sufficiently protracted blood level, whereafter the blood level decreases because the tri-tetracyclines are excreted from the organism like their parent compounds, (most of the tetracyclines are excreted with the urine but doxycycline with faeces as well). The peroral administration of chelocardin is not favourable due to its low absorption value, therefore the parenteral administration in form of a tri-complex has a special advantage. The fact that tri-tetracyclines show no tissue damaging effect, makes not only a treatment by intramuscular administration possible but also by local administration. The results of the various tests performed with tri-tetracyclines in respect of therapeutical activity, sera levels and urinary excretion are detailed in Tables II, III, IV and V.

TABLE II

Means+ and medians+ of MICs of tri-OTC, tri-MOTC, tri-DOOTC and tri-MINO against tetracycline sensitive and tetracycline resistant microorganisms

| Microorganism | tri-OTC | | tri-MOTC | | tri-DOOTC | | tri-MINO | |
|---|---|---|---|---|---|---|---|---|
| | mean μg/ml | median μg/ml | mean μg/ml | median μg/ml | mean μg/ml | median μg/ml | mean μg/ml | median μg/ml |
| Staphylococcus (tetracycline sensitive, 31 strains) | 0.99 | 1 | 0.36 | 0.25 | 0.33 | 0.25 | 0.21 | 0.125 |
| E. coli (tetracycline sensitive, 29 strains) | 1.82 | 2 | 0.99 | 1 | 1.41 | 1 | 0.93 | 0.5 |
| Staphylococcus (tetracycline resistant, 30 strains) | — | — | 36 | 32 | 28 | 8 | 8 | 2 |
| E. coli (tetracycline resistant, 38 strains) | — | — | 58 | 64 | 34 | 34 | 23 | 12 |
| Proteus (tetracycline resistant, 25 strains) | — | — | 69 | 128 | 39 | 32 | 32 | 32 |

+MIC values > 128 are not included in means and medians

TABLE III

Drug concentrations [μg/g] in wet tissues and serum values of rabbits 8 h after i.v. injection of different tri-tetracyclines

| | Doses mg/kg | Number of animals | Serum μg/ml | Lung tissue | Liver tissue | Kidney tissue | Muscle tissue | Spleen tissue |
|---|---|---|---|---|---|---|---|---|
| Tri-OTC[1] | 20 | 6 | 4.7 | 17.5 Sx3.411 p < 0.001 | 27.27 Sx7.543 p < 0.001 | 187 Sx69.54 p < 0.05 | 26.8 Sx10.725 p < 0.02 | 16.53 Sx4.497 p < 0.01 |
| Tri-DOOTC[1] | 15 | 6 | 7.0 | 19.4 Sx1.967 p < 0.001 | 20.82 Sx1.834 p < 0.001 | 56.78 Sx11.376 p < 0.01 | 25.25 Sx3.952 p < 0.01 | 31.95 Sx4.311 p < 0.001 |
| Tri-MOTC | 10 | 4 | 2.6 | 32.1 Sx5.090 p < 0.001 | 26.37 Sx1.332 p < 0.001 | 99.45 Sx43.78 p < 0.05 | 21.15 Sx1.272 p < 0.001 | 40.33 Sx11.643 p < 0.05 |
| Tri-MOTC | 15 | 6 | 6.6 | 27.1 Sx8.295 p < 0.005 | 24.40 Sx3.69 p < 0.001 | 164.20 Sx38.11 p < 0.01 | 18.83 Sx4.01 p < 0.001 | 37.20 Sx2.88 p < 0.001 |
| Tri-MINO | 10 | 6 | — | 58 | 75 | 65 | 60 | 60 |

Sx = Standard error; p = probability.
[1]Preconstituted, ready-for-use injection.

TABLE IV

Sera levels and urinary excretion of Tri-MINO administered intravenously to 13 patients

| Patient No. | Sex | Age | Weight | Duration of therapy (days) | Daily mg · /MINO HCl) | mg/kg | Total mg | Maximum serum level μg/ml | Urinary recovery rate (percent) |
|---|---|---|---|---|---|---|---|---|---|
| 1 | male | 37 | 80 | 1½ | 100 | 1.2 | 150 | 1.8 | 8.3 |
| 2 | male | 27 | 60 | 3 | 2 × 50 | 1.6 | 300 | 2.0 | 19.0 |
| 3 | male | 55 | 60 | 3 | 2 × 50 | 1.6 | 300 | 4.0 | 7.0 |
| 4 | male | 54 | 80 | 1 | 2 × 100 | 2.5 | 200 | 2.0 | 9.0 |
| 5 | female | 27 | 50 | 1 | 2 × 50 | 2.0 | 100 | 2.0 | 15.0 |
| 6 | male | 50 | 80 | 3 | 100 | 1.2 | 300 | — | — |
| 7 | female | 69 | 70 | 3½ | 2 × 100 | 2.8 | 750 | 2.5 | — |
| 8+ | male | 14 | 50 | 3 | 2 × 100 | 4.0 | 600 | — | — |
| 9 | male | 65 | 75 | 2 | 3 × 100 | 2.6 | 400 | 2.3 | 12.0 |

TABLE IV-continued

Sera levels and urinary excretion of Tri-MINO administered intravenously to 13 patients

| Patient No. | Sex | Age | Weight | Duration of therapy (days) | Daily mg · /MINO HCl) | mg/kg | Total mg | Maximum serum level μg/ml | Urinary recovery rate (percent) |
|---|---|---|---|---|---|---|---|---|---|
| 10 | female | 50 | 55 | 4 | 100 | 1.8 | 400 | 2.0 | 13.0 |
| 11 | male | 48 | 88 | 3 | 150 | 1.7 | 450 | 2.5 | 11.0 |
| 12 | male | 30 | 65 | 6 | 150 | 2.3 | 900 | 2.5 | 11.0 |
| 13 | male | 37 | 55 | 5 | 100 | 1.8 | 500 | 2.2 | — |

+infusion

TABLE V

Drug concentration [μg/ml] in sera 30 minutes after the i.v. administration of different Tri-tetracyclines

| | in rabbit | | in human | |
|---|---|---|---|---|
| Tri-TC | doses mg/kg | Serum μg/ml | doses mg | Serum μg/ml |
| Tri-OTC | 20 | 28 | — | — |
| Tri-MOTC | 15 | 35 | 100 | 5.0 |
| Tri-DOOTC | 15 | 30 | 100 | 4.0 |
| Tri-DOOTC | | | 200 | 5.0 |
| Tri-MINO | 10 | 12 | 100 | 2.5 |

The tri-tetracyclines can be applied intrapleurally in the pneumotherapy and are used by a subconjonctival, intraocular (intracameral), intravitreal and intracorneal route of administration in ophthalmology and a favourable therapeutic effect can be obtained without any side-effects. The high aqueous humour level obtained after intravenous administration proves not only the high antibiotic concentration of the extracellular fluid of the human tissues, but simultaneously an opthalmological application becomes possible in clinical cases, showing severe infections, respectively in cases, wherein the considerable extent of the blood circulation of the particular tissue is not favourable for the penetration and accumulation of the locally administered antibiotic compounds.

The application of the preparation of the pharmaceutical compositions containing different complexes of tetracyclines of the invention is exemplified by however, not limited to the following compositions:

EXAMPLE 1

| Ampoule A (dry fill) | 100 mg. | methacycline hydrochloride |
|---|---|---|
| | 82 mg. | tris(hydroxymethyl)-aminomethane hydrochloride |
| | 72 mg. | tris(hydroxymethyl)-aminomethane |
| Ampoule B (dissolving apoule) | 2 ml. | distilled water |

The content of ampoule A is dissolved in the distilled water of ampoule B and the pH of the formed tri-methacycline solution is 7.2. The solution can be administered intravenously, intramuscularly, intrapleurally and intraocularly. After dissolving, the solution can be stored for 48 hours at +4° C.

EXAMPLE 2

| Ampoule A | 100 mg. | minocycline hydrochloride |
|---|---|---|
| Ampoule B | 100 mg. | ascorbic acid |
| | 170 mg. | 1,3-bis-tri(hydroxy-methylamino-propane in 2 ml. of distilled water The pH of the content of ampoule B is adjusted to 9.5 with hydrochloric acid. |

The content of ampoule A is dissolved in the solution in ampoule B. The pH of the thus formed tri-minocycline solution is 6.4. The chloroform/water distribution quotient of this solution is K=19.3 at pH=7.4. As comparison the chloroform/water distribution quotient of the oxytetracycline measured under the same conditions is K=0.008.

Route of administration: intravenous, intramuscular, intrapleural and intraocular.

EXAMPLE 3

5 g. of minocycline hydrocyhloride are dissolved in 100 ml. of aqueous solution containing 10% sucrose, 7.2% of tris(hydroxymethyl)aminomethane, 0.2% of calcium chloride, 0.5% of sodium formaldehyde sulfoxylate. The pH of the thus obtained solution is 8.0. The solution is filled into ampoules in nitrogen atmosphere. The chloroform/water distribution quotient of the so formed tri-minocycline solution is at pH=7.4, K=15.5.

Route of administration: intravenous and intramuscular.

EXAMPLE 4

| Ampoule A | 100 mg. | methacycline hydrochloride |
|---|---|---|
| Ampoule B | 85 mg. | 1,3-bis-tris(hydroxymethyl)methyl-amino-propane in 1 ml. of distilled water (pH = 9.5) |

The content of ampoule A is dissolved in the solution in ampoule B and the pH of the solution of trimethyacycline is 7.0.

Route of administration: intravenous, intramuscular, intrapleural injection, and eye drops.

EXAMPLE 5

| Ampoule A | 100 mg. | demethylchlortetracycline hydrochloride |
|---|---|---|
| Ampoule B | 168 mg. | N—tris(hydroxymethyl)methyl-glycine in 2 ml. of distilled water (pH = 9.0) |

The content of the ampoule A is dissolved in the solution in ampoule B and the pH of the solution of the tri-demethylchlortetracycline is 7.6.

Route of administration: intravenous and intramuscular.

EXAMPLE 6

100 mg. chlortetracycline hydrochloride are dissolved in 8 ml. methanol under a nitrogen atmosphere, 144 mg. Tris are added and the pH is adjusted to 7.9. The solvent is then evaporated under vacuum. The resultant crystalline compound is filled into capsules.

Route of administration: per os.

EXAMPLE 7

| Ampoule A | 50 mg. chelocardin |
| Ampoule B | 72 mg. tris(hydroxymethyl)aminomethane in 2.5 ml. of distilled water (pH = 9.0) |

The content of ampoule A is dissolved in the solution in ampoule B and a solution of pH=8.8 is obtained.

Route of administration: intravenous, intramuscular injections and eye drops.

EXAMPLE 8

200 mg. of methacycline hydrochloride are dissolved in 10 ml. of water containing 850 mg. of 1,3-bis-tris(hydroxymethyl)methylamino-propane and 10 mg. of sodium pyrosulfite and 300 mg. of polyvinylalcohol. The pH of the obtained trimethacycline solution is 6.8.

Route of administration: in the form of eye drops.

EXAMPLE 9

1000 g. of minocycline hydrochloride are dissolved in 1 liter of methanol and under stirring 915 g. of tris(hydroxymethyl)aminomethane in 3 liter of methanol are added. The solution thus obtained is evaporated at reduced pressure under introduction of nitrogen under simultaneous moderate heating of the solution by using an external water bath so that the temperature of the mixture does not exceed 35° C. The dry substance is triturated in 3 l. of ether or benzene and evaporated to dryness.

The melting point of the formed tri-minocycline is 99°-101° C. Tri-minocycline is after trituration with an aprotic solvent a stable pale yellow powder.

What we claim is:

1. A complex of a tetracycline and derivatives thereof and an amino compound containing per molecule at least a tris(hydroxyalkyl) group and at least a primary or secondary amino group, said tetracycline being selected from the group consisting of tetracycline, oxytetracycline, chlortetracycline, methacycline, doxycycline, minocycline, demethylchlortetracycline and chelocardin and acid addition salts thereof and said amino compound being selected from the group consisting of tris(hydroxymethyl)amino methane, 1,3-bis[tris(hydroxymethyl)methylamino]-propane, N-tris(hydroxymethyl)methyl-3-aminopropane sulfonic acid, N-tris(hydroxymethyl)methyl-2-aminomethane sulfonic acid and N-tris(hydroxymethylmethylglycine and salts thereof.

2. A process for preparing a therapeutically active tetracycline complex comprising reacting a tetracycline compound selected from the group consisting of tetracycline, oxytetracycline, methacycline, doxycycline, minocycline, demethylchlor tetracycline, chlortetracycline, chelocardin and acid addition salts thereof with a molar excess of an amino compound selected from the group consisting of tris(hydroxymethyl)aminomethane, 1,3-bis-(tris(hydroxymethyl)methylamino)-propane, N-tris(hydroxymethyl)methyl-3-aminopropane sulfonic acid, N-tris(hydroxymethyl)methyl-2-aminoethane sulfonic acid, N-tris(hydroxymethyl)methyl glycine and salts thereof, to produce said complex.

3. A process according to claim 2 which comprises adjusting the pH of the complex to a value in the range of 6.8 to 8.8.

4. A process according to claim 2 which comprises reacting the amino compound with tetracycline compound dissolved in an aqueous or organic solvent.

5. A process, according to claim 2, wherein at least a three fold molar excess of the amino compound is employed.

6. A process, according to claim 2, wherein a three to six fold molar excess of the amino compound is employed.

7. A therapeutic composition comprising a tetracycline and an amino compound containing per molecule at least a tris(hydroxyalkyl) group and at least a primary or secondary amino group in a molar excess in respect to the tetracycline compound said tetracycline being selected from a group consisting of tetracycline, oxytetracycline, chlortetracycline, methacycline, doxycycline, minocycline, demethylchlortetracycline, and chelocardin and acid addition salts thereof and the said amino compound being selected from the group consisting of tris(hydroxymethylamino)methane, 1,3-bis[tris(hydroxymethyl)methylamino]propane, N-tris(hydroxymethyl)methyl-3-aminopropane sulfonic acid and N-tris(hydroxymethyl)2-aminomethane sulfonic acid and N-tris(hydroxymethyl)methylglycine, and salts thereof and a pharmaceutically carrier therefor.

8. The composition according to claim 7, wherein said carrier is a vehicle suitable for parenteral administration to mammals.

9. A method for inhibiting growth of a micro-organism responsive to tetracycline antibiotic therapy, in a mammal infected by said microorganism, comprising administering to said mammal an amount effective to inhibit the growth of said micro-organism of a complex of a tetracycline and an amino compound containing per molecule at least a tris(hydroxyalkyl) group and at least a primary or secondary amino group in respect to the tetracycline compound said tetracycline being selected from a group consisting of tetracycline, oxytetracycline, chlortetracycline, methacycline, doxycycline, minocycline, demethylchlortetracycline, and acid addition salts thereof, and chelocardin and said amino compound being selected from the group consisting of tris(hydroxymethyl)-aminomethane, 1,3-bis[tris(hydroxymethyl)methylamino]-propane, N-tris(hydroxymethyl)methyl-3-aminopropane sulfonic acid and N-tris(hydroxymethyl)2-aminomethane sulfonic acid and N-tris(hydroxymethyl)methylglycine and salts thereof.

* * * * *